Feb. 23, 1960 A. FRYER Plant Pat. 1,917
ROSE PLANT
Filed May 15, 1959
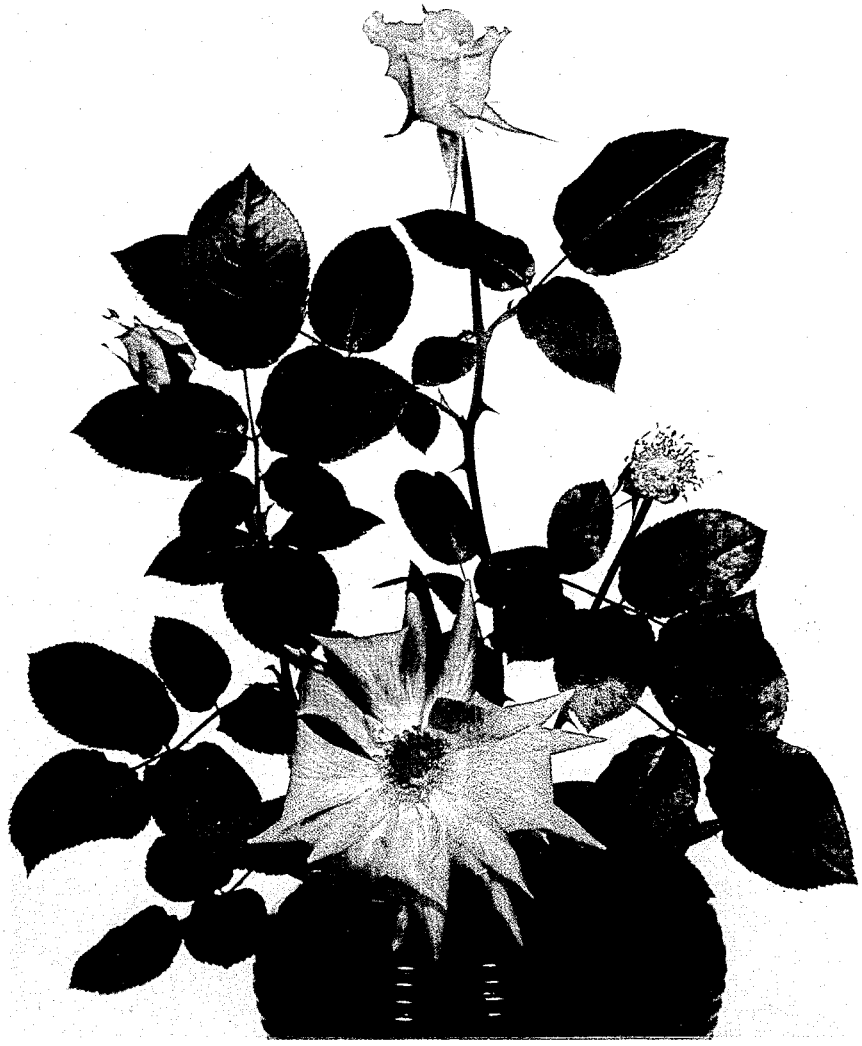
Inventor.
Arthur Fryer
By: Robb & Robb
Attorneys.

United States Patent Office

Plant Pat. 1,917
Patented Feb. 23, 1960

1,917

ROSE PLANT

Arthur Fryer, Knutsford, England, assignor, by mesne assignments, to Eldon Pinkeney Dering, doing business as Peterson & Dering, Scappoose, Oreg.

Application May 15, 1959, Serial No. 813,613

1 Claim. (Cl. 47—61)

The present invention relates to a new and distinct variety of rose plant of the hybrid tea class, which originated as a sport of the variety "Doreen" (unpatented).

The new sport was discovered by me amongst a block of Doreen plants which were being grown under my supervision and control on property of the nursery of which I was a director, said property being located at Knutsford, Cheshire, England. In the course of growing plants of Doreen, as referred to above, my attention was attracted to one particular plant which appeared to be bearing flowers distinctly different from those of the normal flowers of Doreen, as evidenced by the fact that the flowers were a reverse-bicolor, contrary to those of the parent variety. Upon closer examination of this plant, I found that it had sported, and I thereupon took steps to preserve the sport, keep it under observation, and later to asexually reproduce the same. Continued observation of the original plant and the asexual reproductions thereof, as performed by budding at Knutsford, England, fully confirmed that the flowers of the sport were a distinct reverse-bicolor, with scarlet red on the inside of the petals, and golden yellow on the outside of the petals, these colors merging into a brilliant orange as the flowers open.

In general, the new sport has a plant habit that is similar to the parent variety "Doreen," said plant being upright, of ordinary vigor, medium height, and with the foliage well-distributed on the plant. The flowers usually occur singly but sometimes in clusters of as many as 6 flowers, on stems of medium length, and the flowering habit is fairly continuous and prolific during the growing season.

Asexual reproduction of the new variety, by budding as aforesaid, shows that these characteristics come true to form, and definitely differentiate the new sport from its parent, as well as from all other varieties of which I am aware.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with Robert Ridgway's Color Standards and Nomenclature (hereinafter abbreviated as "Ridgway"), Robert F. Wilson's Horticultural Colour Chart (hereinafter abbreviated as "Wilson"), and the Nickerson Color Fan (hereinafter abbreviated as "Nickerson"), as indicated, except where color terms of ordinary dictionary significance are obvious:

Type: Hardy; medium tall bush; for outdoor cut flowers and for garden decoration.
Class: Hybrid tea.
Parentage: Sport of "Doreen."
Propagation: Holds its distinguishing characteristics through succeeding propagations by budding.

*Flower*

Locality where grown and observed: Scappoose, Oregon, U.S.A., and Knutsford, England.
Flowers borne: Usually singly, but sometimes in clusters of as many as 6; on stems of medium length and normal strength.
Quantity of bloom: Free.
Continuity: Continuous during growing season.
Fragrance: Strong. Nature—sweet.
Bud:

*Peduncle.*—Medium length (from 8 to 9 cm.); medium heavy (about 3 mm.); erect; rough; with numerous reddish gland-tipped cilia and reddish gland-tipped prickles. Color—between Moderate Yellow Green, Plate 5 GY 5/6 (Nickerson) and Strong Yellow Green, Plate 5 GY 6/8 (Nickerson).

*Before calyx breaks.*—Size—medium large (about 5.5 cm., including receptacle and foliaceous appendages, x 1.7 cm.). Form—long pointed; with conspicuous neck; with long, slender, moderately cut foliaceous parts extending beyond the tip of the bud equal to ½ or more of its length; with numerous gland-tipped cilia on surface of bud. Color—near Moderate Yellow Green, Plate 5 GY 5/6 (Nickerson) or slightly darker.

*As calyx breaks.*—Color (exposed petal)—near Deep Chrome, Plate III, 17.O–Y.b (Ridgway), sometimes flushed with near Nopal Red, Plate I, 3.O–R.i (Ridgway).

*As first petal opens.*—Size—medium large. Form—long pointed. Color: outside—Indian Yellow, Plate 6, page 6 (Wilson), sometimes irregularly flushed Signal Red, Plate 719, page 93 (Wilson) near apex; inside—base Indian Yellow, Plate 6, page 6 (Wilson) to height equal to about ⅕ the distance from base to apex; Orient Red, Plate 819, page 165 (Wilson), or darker, above.

*Opening.*—Opens up well in all weather.

Bloom:

*Size (when fully open).*—From 4½ inches to 5½ inches.

*Petalage.*—Double; from 28 to 35 petals; arranged regularly.

*Form.*—Full and high-centered at first, becoming open, but not flat, as it nears senescence; petals at first being moderately cupped, with short, very tight roll outward at apical-lateral edges, but later becoming tightly rolled outward along lateral edges, and almost quilled.

Petals:

*Texture.*—Medium thickness; leathery. Inside—velvety. Outside—satiny.

*Shape.*—Outside—nearly round, with margin and apex entire. Intermediate—from broad obovate to nearly round, with apex and margin entire. Inside—obovate, with apex and margin entire.

This description of a newly opened flower was made from a rose grown in a greenhouse in the month of March at Scappoose, Oregon, U.S.A.:

*Color.*—Outer petal: outside surface—Indian Yellow, Plate 6, page 6 (Wilson) at base, becoming gradually lighter upward to from Indian Yellow, Plate 6/1, page 6 (Wilson) to Indian Yellow, Plate 6/2, page 6 (Wilson) at apex; frequently irregularly flushed Mandarin Red, Plate 17/1, page 17 (Wilson) near apex; inside surface—base Lemon Yellow, Plate 4, page 4 (Wilson) to a height equal to ¼ to ⅕ the distance from base to apex, blending very sharply upward to Dutch Vermilion, Plate 717, page 156 (Wilson) and becoming gradually lighter and more red upward to Vermilion, Plate 18/1, page 18 (Wilson) near apex. Intermediate petal: outside surface—Indian Yellow, Plate 6, page 6 (Wilson) at base, becoming gradually lighter upward to Indian Yellow, Plate 6/1, page 6 (Wilson) near apex; near the edges of petal, the red pigment from the inside surface of the petal may show through, giving the impression of a red flush; inside surface—base Lemon Yellow, Plate 4, page 4 (Wilson) to a height equal to from ¼ to ⅕ the distance from base to apex, blending very sharply upward to Orient Red, Plate 819, page 165 (Wilson), or between Orient Red, Plate 819, page 165 (Wilson) and Dutch Vermilion, Plate 717, page 156 (Wilson), and gradually lightening slightly to from near Orient Red, Plate 819/1, page 165 (Wilson) to Plate 819/2, page 165 (Wilson) toward apex. Inner petal: outside surface—Indian Yellow, Plate 6, page 6 (Wilson) at base, becoming gradually lighter upward to Indian Yellow, Plate 6/1, page 6 (Wilson) near apex; near the edges of petal, the red pigment from the inside surface of the petal may show through, giving the impression of a red flush; inside surface—base Lemon Yellow, Plate 4, page 4 (Wilson) to a height equal to from ¼ to ⅕ the distance from base to apex, blending very sharply upward to Orient Red, Plate 819, page 165 (Wilson), or between Orient Red, Plate 819, page 165 (Wilson) and Dutch Vermilion, Plate 717, page 156 (Wilson), and gradually lightening slightly to from near Orient Red, Plate 819/1, page 165 (Wilson) to Plate 819/2, page 165 (Wilson) toward apex.

This description was made from a rose that was open for 3 days in a greenhouse in the month of March, at Scappoose, Oregon, U.S.A.:

*Color.*—Outer petal: outside surface—Lemon Yellow, Plate 4, page 4 (Wilson) at base, becoming gradually and continuously lighter and more red upward to Indian Yellow, Plate 6/3, page 6 (Wilson) at apex; predominant color near Lemon Yellow, Plate 4/2, page 4 (Wilson); inside surface—base Lemon Yellow, Plate 4, page 4 (Wilson) to a height equal to from about ¼ to ⅕ the distance from base to apex, blending upward to Mandarin Red, Plate 17/2, page 17 (Wilson) and becoming gradually paler and more blue upward to Scarlet, Plate 19/3, page 19 (Wilson) near apex; pigmentation remains more intense along veins. Intermediate petal: outside surface—Buttercup Yellow, Plate 5, page 5 (Wilson) at base, fading smoothly upward to from Buttercup Yellow, Plate 5/2, page 5 (Wilson) to Buttercup Yellow, Plate 5/3, page 5 (Wilson) near apex, with predominant color Buttercup Yellow, Plate 5/2, page 5 (Wilson); inside surface—base Lemon Yellow, Plate 4, page 4 (Wilson) to a height equal to from about ¼ to ⅕ the distance from the base to apex, blending upward sharply to Vermilion, Plate 18/1, page 18 (Wilson), fading gradually upward to Vermilion, Plate 18/2, page 18 (Wilson) and becoming more blue to Scarlet, Plate 19/2, page 19 (Wilson) near apex. Inner petal: outside surface—Buttercup Yellow, Plate 5, page 5 (Wilson) at base, fading smoothly upward to from Buttercup Yellow, Plate 5/2, page 5 (Wilson) to Buttercup Yellow, Plate 5/3, page 5 (Wilson) near apex, with predominant color Buttercup Yellow, Plate 5/2, page 5 (Wilson); inside surface—base Lemon Yellow, Plate 4, page 4 (Wilson) to a height equal to from about ¼ to ⅕ the distance from the base to apex, blending upward sharply to Vermilion, Plate 18/1, page 18 (Wilson), fading gradually upward to Vermilion, Plate 18/2, page 18 (Wilson) and becoming more blue to Scarlet, Plate 19/2, page 19 (Wilson) near apex.

*General color effect.*—Newly opened flower—sharp reverse-bicolor, Dutch Vermilion, Plate 717, page 156 (Wilson) with Indian Yellow, Plate 6, page 6 (Wilson). 3-days open—from Scarlet, Plate 19/1, page 19 (Wilson) to Scarlet, Plate 19/2, page 19 (Wilson).

*Behavior.*—Petals drop off cleanly; fading and becoming somewhat blue in hot, dry weather.

*Flower longevity.*—Cut roses grown in greenhouse and kept at living-room temperatures—4 days in March.

*Reproductive organs*

Stamens: medium number; arranged regularly immediately within the corolla, between the corolla and the lip of the receptacle.

Filaments: Medium length (from 8 to 12 mm.); almost all with anthers. Color—near Pomergranate Purple, Plate XII, 71.V–RR.i (Ridgway).

Anthers: Medium size; all open at nearly same time. Color—near Light Cadmium, Plate IV, 19.YO–Y. (Ridgway).

Pollen: Abundant. Color—near Deep Chrome, Plate III, 17.O–Y.b (Ridgway).

Pistils: Medium number.

Styles: Quite even; medium length; medium caliper; loosely bunched.

Stigma: Color—yellow.

Ovaries: Enclosed in receptacle.

Hips: Medium size; obovate; without conspicuous neck; moderately smooth; walls medium thickness and fleshy. Color—variable with environment and degree of maturity, but generally orange.

Seeds: Moderately numerous; medium size.

Sepals: Persistent; medium large (1 x 4.5 cm.); slightly spear-shaped, but nearly straight-sided; folded straight down. Color—near Scheeles Green, Plate 860/1, page 175 (Wilson).

*Plant*

Foliage:

*Leaves.*—Compound of usually 5 leaflets; abundant; medium large (7.5 x 4.5 cm.); moderate substance; leathery; glossy.

*Leaflets.*—Ovate, with apex mucronate. Base—rounded. Margin—doubly serrate.

*Color.*—Mature: upper surface—between Parsley Green, Plate 00962, page 193 (Wilson) and Spinach Green, Plate 0960, page 187 (Wilson); under surface—near Spinach Green, Plate V, 29.GG–Y.m (Ridgway). Young: upper surface—near Scheeles Green, Plate 860, page 175 (Wilson) or darker; in early stages flushed laterally with near Oxblood Red, Plate 00823, page 191 (Wilson); under surface—near Asphodel Green, Plate XLI, 29'''.GG–Y. (Ridgway); in early stages, especially in rapid vigorous growth, flushed laterally with near Deep Livid Brown, Plate XXXIX, 1'''.RED.i (Ridgway); one entire side may be flushed in this manner, while on the other side of the mid-rib the flush may be slight or partial.

*Rachis (the supporting stem of the compound leaf).*—Medium heavy. Upper side—deeply grooved; several glandular cilia along lateral ridges. Under side—with few to several relatively large thorns.

*Stipules.*—Moderately long (up to 2 cm., including points); slender (5 mm.); with medium long points turning out at an angle of 45° or less.

*Disease resistance.*—Subject to mildew, as determined by comparison with other varieties grown under comparable cultural conditions at Scappoose, Oregon, U.S.A.

Growth:

*Habit.*—Bushy; moderately branched.

*Growth.*—Moderate.

*Canes.*—Medium caliper.

*Main stems.*—Color—Dull Green, near Deep Dull Yellow-Green (1), Plate XXXII, 31".Y–G.k (Ridgway), usually with corky brown overlay. Thorns—Several; medium long (from 1 to 1.5 cm.); hooked slightly downward; base moderate (to about 4 x 12 mm.). Prickles—usually none. Hairs—none.

*Branches.*—Color—near Deep Dull Yellow-Green (1), Plate XXXII, 31".Y–G.k (Ridgway). Thorns—from several to many; medium long (1 cm.); hooked downward; base moderate (3 x 8 mm.). Prickles—usually several; color—reddish. Hairs—Usually several glandular cilia; color—reddish.

*New shoots.*—Color—reddish at first, near Diamine Brown, Plate XIII, 3'.O–R.m (Ridgway), gradually flushed green to near Cress Green, Plate XXXI, 29".GG–Y.k (Ridgway). Thorns—several; medium long (1 cm.); hooked downward; with base frequently short (1 x 3 mm.). Prickles—few; color — reddish. Hairs — usually few glandular cilia.

I claim:

A new and distinct variety of rose plant of the hybrid tea class, substantially as herein shown and described, characterized particularly as to novelty by the unique combination of a plant habit generally similar to that of the variety "Doreen" (unpatented), and the good shape, strong, sweet fragrance and distinctive reverse-bicolor of the flowers, with scarlet red color inside and golden yellow color outside of the flower petals, said colors merging into a brillint orange as the flowers open.

No references cited.